United States Patent [19]

Okrasinski et al.

[11] Patent Number: 5,399,752
[45] Date of Patent: Mar. 21, 1995

[54] PURIFICATION OF CARBOXYL STREAMS

[75] Inventors: Stanley J. Okrasinski, Kingsport; Regina M. Moncier, Church Hill; Patricia N. Mercer, Kingsport; Dewey W. Fuller, Jr., Bristol; Steven L. Cook, Kingsport, all of Tenn.

[73] Assignee: Eastman Chemical Company, Kingsport, Tenn.

[21] Appl. No.: 251,167

[22] Filed: May 31, 1994

[51] Int. Cl.⁶ .............................................. C07C 51/42
[52] U.S. Cl. .................................... 562/608; 562/548; 562/599; 560/248
[58] Field of Search ............... 562/608, 595, 598, 599, 562/548; 560/248

[56] References Cited

U.S. PATENT DOCUMENTS

| 4,036,940 | 7/1977 | McLane et al. | 423/503 |
| 4,087,623 | 5/1978 | Sherwin et al. | 560/246 |
| 4,664,753 | 5/1987 | Erpenbach et al. | 562/248 X |

Primary Examiner—Arthur C. Prescott
Attorney, Agent, or Firm—J. Frederick Thomsen; John F. Stevens

[57] ABSTRACT

Disclosed is a process for the purification of carboxyl streams such as product streams comprising one or more carboxyl compounds selected from carboxylic acids, carboxylic anhydrides and alkylidene dicarboxylates. The process provides a means for the reduction of the iodine content of carboxyl compound product streams which are contaminated with one or more iodine compounds.

15 Claims, No Drawings

PURIFICATION OF CARBOXYL STREAMS

This invention pertains to the purification of carboxyl streams such as product streams comprising one or more carboxyl compounds selected from carboxylic acids, carboxylic anhydrides and alkylidene dicarboxylates. More specifically, this invention pertains to a process for the reduction of the iodine content of carboxyl compound product streams which are contaminated with one or more iodine compounds.

Various processes for the preparation of carboxylic acids and anhydrides, including the coproduction of carboxylic acids and anhydrides or carboxylic anhydrides and alkylidene dicarboxylates, by the catalytic carbonylation of alcohols, ethers, esters and/or olefins have been described extensively in the literature and, in some cases, have been used on a commercial scale. Typically, these carbonylation processes are carried out in the presence of a Group VIII metal and an iodine-containing compound such as, but not limited to, hydrogen iodide, an alkyl iodide such as methyl iodide, a phosphonium iodide, an alkali metal iodide, or an iodide salt of a number of other catalyst or promoter components. See, for example, S. W. Polichnowski, J. Chem. Educ., 1986, 63, 206 and U.S. Pat. Nos. 3,769,329, 4,374,070, 4,661,631 and 4,994,608. The carboxyl product-containing reactor effluents from such carbonylation processes commonly are subjected to conventional separation procedures, such as fractional distillation, which allows the recovery and recycle of both the volatile and non-volatile iodine containing compounds. Indeed, the economic operation of such processes depends, in part, upon such an effective recycle. In spite of the efficiency of most separation methods, however, small amounts of iodine-containing compounds, e.g., up to about 250 parts per million by weight (ppmw) [I], typically are contained in the product. For certain end uses, purchasers require that the iodine content of carboxyl compounds be extremely low, e.g., <20 parts per billion by weight (ppbw).

U.S. Pat. No. 4,792,420 discloses the use of expensive Group VIII, noble metal-containing catalysts in conjunction with hydrogen to reduce the level of iodine-containing impurities in carboxylic acid anhydride streams to a very low level. This patent specifically excludes streams that consist primarily of acetic acid, i.e., expressly limiting components other than carboxylic acid anhydrides to 25 weight percent or less of the total, and indicates that anhydrous conditions are to be employed.

European Patent Application Publication 372,993 describes the improvement of acetic acid permanganate times by treatment with hydrogen and a hydrogenation catalyst containing platinum, palladium, rhodium, ruthenium, osmium, iridium, nickel, or cobalt. Copper-containing catalysts are not mentioned and iodine levels are not determined. There is no specific teaching that the method will reduce the iodine content to <20 ppb and, in fact, mentions that the described method is useful in conjunction with other iodine removal methods. This patent primarily teaches the reduction of aldehydes and unsaturated aldehydes to the saturated aldehyde and/or alcohol, thus reducing the level of oxidizable material. The only analytical method reported is permanganate time.

Canadian Patent 1,234,149 (equivalent to EP 143,179) describes the treatment of acetic acid or acetic anhydride at 50° to 200° C. preferably 80° to 140° C., with hydrogen in the presence of a Group VIII noble metal such as ruthenium, osmium, iridium or, preferably rhodium, palladium or platinum finely distributed on a silica or alumina support. This treatment is said to reduce the iodine content, present as alkyl or aryl iodides and hydrogen iodide or phosphonium iodide salts, to acceptable, e.g., <20 ppbw, levels. The residence time is 0.2 to 6 hours and treatment is carried out at a pressure of 0.5 to 10 bars. The catalyst is preferably separated by filtration and is discarded when its capacity is exhausted. A comparative example reveals that iodine removal is not acceptable when hydrogen is omitted.

Canadian Patent 1,279,655 (equivalent to EP 217,182) discloses an improvement to the process disclosed in CA 1,234,149 which involves the addition of carbon monoxide to the gaseous feed to overcome a serious defect. Apparently, in the absence of added carbon monoxide, catalyst activity decreases relatively rapidly, and efficient iodine removal then requires that the operating temperature of the catalyst bed be increased. At these increased temperatures excessive by-product formation (acetaldehyde, acetic acid and ethylidene diacetate when the stream being treated contains acetic anhydride) occurs. It was found that if the gas fed to the treating bed contains carbon monoxide then the formation of these reduced byproducts could be minimized.

The use of a heterogeneous noble metal catalyst according to the known processes cited above presents at least two significant disadvantages. The first is the cost of the noble metal catalysts. This is of particular concern as the catalyst is discarded when exhausted. Furthermore, in the above-described process, in order to maintain catalyst activity and avoid side-reactions, both hydrogen and carbon monoxide must be present in the stream to be treated. This increases both the complexity of the system and its cost.

U.S. Pat. No. 4,664,753 discloses a method for iodine removal from acetic acid, acetic anhydride and/or ethylidene diacetate streams at a temperature of 20° to 250° C. The disclosed method requires a two component system consisting of (i) a phosphine or amine and (ii) zinc or compounds of zinc, copper, silver or cadmium. Treatment with this two-component system is followed by distillation. These chemical traps might be placed in a still bottom and continuously circulated through a reboiler. Contact (residence) times of 15 to 120 minutes are required and continuous replenishment is possible.

The process proposed in U.S. Pat. No. 4,664,753 utilizes a chemical trap comprising a two-component system which degrades with time. Furthermore, the materials formed by the reaction of the chemical traps with iodine or organic iodine-containing species may not be stable to the conditions of prolonged use. Furthermore, prolonged residence of active components of the chemical traps in the reboiler of the distillation train likely would result in fouling.

Finally, U.S. Pat. No. 4,036,940 describes the use of a single type of catalyst (copper oxide/chromium oxide on alumina) for the recovery and recycle of iodine from hydrocarbon streams. This patent does not mention the removal of iodine from a carboxyl stream. The process disclosed requires either a catalyst activation step carried out at 400°–450° C. (during which process hydrogen or carbon monoxide is passed over the bed resulting in the catalyst turning a bright red color) or one of these reductants is passed over the bed concurrently with the vaporized hydrocarbon stream being treated. During operation, the iodine removal bed is maintained in the temperature range of 300°–500° C. and is able to retain 85.9–93.7% of the iodine flowing through it.

The disadvantages of the process disclosed in U.S. Pat. No. 4,036,940 include:

(1) The high temperatures required for activation (400°–450° C.) and operation (300°–500° C.) of the process since such high temperatures (a) are incompatible with maintaining a high surface area catalyst (the bright red color of the reduced catalyst reported in this patent is characteristic of a highly sintered material); (b) require a process stream containing acetic acid/anhydride to be heated well beyond the point at which they become vapor and, thus, are economically unattractive; and (c) are incompatible with streams containing acetic anhydride as this material is unstable at such temperatures.

(2) In spite of (or possibly because of) the high operating temperatures required in the process of U.S. Pat. No. 4,036,940, the highest demonstrated efficiency for iodine removal is 93.7%. This efficiency level is inadequate for producing acetic acid/anhydride streams that meet appropriate fitness-for-use criteria.

The process of the present invention represents a highly-efficient means for the removal of iodine and its compounds from streams that contain one or more carboxyl compounds selected from carboxylic acids, carboxylic anhydrides and alkylidene dicarboxylates. The present invention provides a process for the reduction in the iodine content of a crude carboxyl product stream comprising (i) one or more carboxyl compounds selected from carboxylic acids, carboxylic anhydrides and alkylidene dicarboxylates and (ii) iodine, one or more iodine-containing compounds or a mixture thereof, which comprises the steps of:

(1) contacting the crude carboxyl stream, optionally in the presence of hydrogen, with a copper-containing scavenger material in an iodine removal zone; and (2) removing from the iodine removal zone a refined carboxyl product stream containing less iodine than the crude carboxyl stream.

The process of this invention represents an improvement over the existing art as it (1) avoids the use of expensive noble-metal catalysts, (2) operates at moderate temperatures thus providing both an economic advantage as well as being compatible with the presence of acetic anhydride in the stream being treated, and (3) provides a means to ameliorate problems arising from the presence of small amounts of oxygen in the stream being treated. During the operation of the above-described process, the passage of the iodine-containing species through the copper-containing scavenging material is believed to result in an iodine/copper reaction.

The carboxyl residues of the carboxylic acids, carboxylic anhydrides and alkylidene dicarboxylates referred to herein may contain from 2 to about 6 carbon atoms and, as mentioned hereinabove, may be derived from alcohols, ethers, esters and/or olefins using known carbonylation processes. Similarly, the alkylidene radical of the alkylidene dicarboxylates also may contain from 2 to about 6 carbon atoms. However, the crude carboxyl product stream subjected to the purification process of the present invention more typically will be an acetyl product stream comprised of acetic acid, acetic anhydride, a mixture of acetic acid and acetic anhydride (resulting from the co-production of acetic acid and acetic anhydride or the use of acetic acid as a process solvent in the manufacture of acetic anhydride) or a mixture of acetic acid, acetic anhydride and ethylidene diacetate. The present process is particularly suitable for the reduction in the iodine content of crude carboxyl streams comprising acetic acid.

The crude carboxyl product stream normally is obtained from a carbonylation production system wherein an alcohol, ether, ester and/or olefin is contacted with carbon monoxide in the presence of a metal catalyst (Group VIII or a suitable non-noble metal compound), iodine and/or an iodine compound and, optionally, one or more promoters or primary catalyst stabilizers. The use of iodine in the carbonylation process leads to the formation of various iodine species, depending in part upon the various materials which may be included in the particular catalyst system or combination in use. Such iodine-containing impurities may comprise an alkyl iodide, e.g., methyl or ethyl iodide; an aryl iodide, e.g., phenyl iodide; hydrogen iodide; iodine; a quaternary ammonium or phosphonium iodide; an iodide salt of a transition metal such as rhodium, iron, chromium, nickel, molybdenum, etc.; an iodide salt of an alkali or alkaline earth metal such as sodium, lithium, potassium, beryllium, magnesium, or calcium; an alkyl iodocarboxylic acid, e.g., methyl iodoacetate; or an iodoalkyl carboxylate, e.g., iodomethyl acetate. The iodine content of the crude carboxyl stream may be as high as 10 weight percent but normally is in the range of about 500 ppbw to 250 parts per million by weight (ppmw). Usually the iodine removal process of the invention will reduce the iodine content of the refined carboxyl product stream to less than about 200 ppbw, preferably to less than 20 ppbw.

Other materials which may be present in the crude carboxyl product stream used as the feedstock in the process of this invention include an alcohol, an alkyl carboxylate ester, a dialkyl ether, water or other materials endogenous to catalytic carbonylation processes. Normally, the carboxyl compounds will constitute at least 50 weight percent, preferably 75 weight percent of the crude carboxyl product stream. It is apparent to those skilled in the art that the iodine removal method can be applied to any product stream from which it is necessary to remove or recover iodine-containing components.

The temperature and pressure maintained within the iodine removal zone may vary substantially depending on numerous factors such as whether the process is operated in a liquid or vapor phase, the particular copper scavenging material employed, the concentration of iodine in the crude carboxyl feed, the degree of purification desired, etc. For example, temperatures and pressures in the range of about 20° to 275° C. and about 0.25 to 10 bars (absolute) may be required for certain carboxyl streams. When the carboxyl stream is comprised of acetyl components, the temperature will be about 80° to 250° C., preferably 120° to 250° C. The pressure may be moderately above or below atmospheric but typically is slightly above as a result of the pressure generated within the vessel containing the iodine removal zone.

A broad range of copper-containing materials are effective in reducing the concentration of iodine-containing impurities in accordance with the present invention. The majority of these materials are available commercially as catalysts and are referred to herein as such. The capacity of these materials to remove iodine-containing impurities from process streams depends upon such factors as the amount of copper present on the catalyst, and the ability to transport the iodine impurities to the active copper surface. The copper-containing materials may be selected from copper articles such as copper gauze, and unsupported and supported copper-containing catalysts. Copper chromite is typical of the unsupported catalysts. The supported catalysts comprise copper deposited on a catalyst support material such as alumina, silica, alumina/silica, carbon, titania, titania/alumina, titania/silica, or titania/alumina/silica. The copper content of such supported catalysts may be in the range of about 0.5 to 60 weight percent.

Since copper catalysts generally are received in the oxidized form, it is necessary to reduce these materials before use. After this preactivation step, the organic and gaseous feeds are allowed to flow through the iodine removal zone. The flow rates for the crude carboxyl product stream vapor mixture may be varied substantially and are, in part, determined by the particular copper-containing material used, the surface area and geometric configuration of the copper-containing material and the degree of iodine removal which is desired. Thus, beds of copper catalysts can be simply designed by accepted engineering practices and the scope of the current invention is not to be limited by the particular bed configuration. The flow rate of the carboxyl product stream through the iodine removal zone, for both liquid and vapor phase operation, is given herein as a liquid hourly space velocity (LHSV), i.e., liquid volume unit of crude carboxyl product stream per hour per volume unit of catalyst. Typical LHSV values for the crude carboxyl product stream are within the range of about 0.1 to 13.

After passage through the iodine removal zone, the effluent, whether vapor or liquid, may be cooled to allow the collection of the purified carboxyl product stream. Alternately, the effluent may be fed directly to the inlet of a distillation column or other additional purification device or system. It should be obvious that the purification method described herein can be used in conjunction with other purification steps, and that these may be intermingled with the current invention in any order.

Generally, it is advantageous to avoid the introduction of oxygen to the iodine removal zone. Its presence results in the formation of copper oxide as well as copper(I) carboxylate salts. These latter materials have been found to migrate (sublime) from the iodine removal zone, resulting in the contamination of the refined carboxyl stream. Thus the presence of oxygen would impose a limitation upon the current method if there were no means to abate these effects. If small amounts of oxygen are present in the stream being treated then the purification process of this invention is preferably carried out in the presence of hydrogen. The purpose of the hydrogen is to maintain the copper in a reduced state and thereby suppress the migration (sublimation) of copper(I) carboxylate from the iodine removal zone. Under such conditions the presence of hydrogen avoids any significant contamination of the refined stream.

The presence of hydrogen might also continuously reduce any copper oxide formed by the introduction of oxygen to metallic copper and water (if this is the desired action then carbon monoxide might also be utilized and carbon dioxide would be formed). It should be noted that this introduces additional quantities of water into the product stream. While streams obtained from typical carbonylation processes will be free from significant quantities of oxygen, circumstances might arise, particularly in the treatment of other streams, in which this aspect of the present invention enables its effective use.

The hydrogen employed in the process may be pure hydrogen or it may contain impurities or diluents such as carbon monoxide, argon, helium, and the like. The quantity of hydrogen provided to the iodine removal zone can be varied over a wide range. As mentioned hereinabove, in the known processes which utilize a noble-metal catalyst, the presence of hydrogen is essential to effect efficient iodine removal. However, in the present invention hydrogen is required only to avoid significant copper contamination of the treated carboxyl product when the untreated stream contains small amounts of oxygen. Thus, the only flow requirement for the hydrogen component of the feed stream is that it be sufficient to suppress significant migration of copper from the iodine removal zone. For example, the volume:weight ratio of the hydrogen to crude carboxyl product stream may be in the range of about 0.1:1 to 15,000:1 but normally will be in the range of about 1:1 to 1000:1. Typical gas hourly space velocities for the hydrogen feed are within the range of about 0.2 to 30.

Another preferred embodiment of the invention includes operating the process in the vapor phase wherein the crude carboxyl product stream is vaporized in a heated zone or obtained as a vapor stream from either a reaction zone, distillation column reboiler, or distillation column side-draw. The temperature of this feed stream is kept sufficiently high (usually 120° to 250° C.) to maintain it in the vapor state and is otherwise only important in the effect it has upon the temperature of the iodine removal zone. Likewise, while the pressure of this stream is typically slightly above atmospheric, it can be maintained over a wide range and is dependent only upon the requirement to maintain the feed stream in the vapor phase. As mentioned hereinabove, the LHSV for the flow rate of the carboxyl product stream in gas phase operation is within the range of about 0.1 to 13.

The process of the present invention is further illustrated by the following examples. The experimental apparatus consisted of a preheater and iodine removal zone containing a solid copper-containing material, a condenser, and a collection flask. The preheater was constructed of a glass tube approximately 33 cm long having an interior diameter of 2.5 cm with a concentric 6 mm diameter thermowell along its length, contained quartz chips and was electrically heated. The purpose of the preheater was to either preheat or to vaporize the crude carboxyl product stream prior to its entry into the iodine removal zone. The temperature of the preheater was maintained at 180° C.

The iodine removal zone was constructed of a glass tube/thermowell assembly having the same dimensions as the preheater. The central 18 cm section of the iodine removal zone assembly contained the copper-containing material being tested. Quartz chips were packed on either side of the copper-containing material, filling the remainder of the glass tube. The assembly was electrically heated and its temperature was maintained at 180° C. The outlet of the iodine removal zone fed into an air-cooled condenser, which allowed the collection of the liquid product.

Prior to the commencement of the crude carboxyl product feed to the apparatus, air was removed from the system by purging with argon. The air removal step was followed by activation of the copper-containing catalyst by a pre-reduction step wherein an 8 volume percent hydrogen in nitrogen mixture was passed at a rate of 50 mL per minute slightly above 1 atmosphere pressure through the experimental assembly. The initial temperature of the reactor was 180° C. and throughout the activation process a careful watch was maintained to ensure that a reaction exotherm did not raise the temperature of the system to a point which threatened to cause sintering of the catalyst. At no time was the temperature of the iodine removal zone allowed to rise above 210° C. Water was evolved during the activation process giving positive indication that any oxides present on the copper catalysts were being reduced. This pre-activation step was continued for several hours after all signs of water evolution ceased. Upon visual examination, the copper-containing catalyst exhibited the intense black color that is typically characteristic of a finely dispersed reduced copper.

Control Example 1

Quartz chips (75 mL) were placed within the iodine removal zone and, after assembly, air was removed from the system by purging with argon. Then an 8% hydrogen in nitrogen mixture was passed through the bed at 50 mL per minute and the temperature raised to 180° C. An acetic acid stream containing 5 ppm hydriodic acid (prepared using glacial acetic acid and 50% hydriodic acid) was then fed at 13 mL (liquid) per hour. The effluent vapor stream was cooled and the product collected. The analysis of five samples, collected at one hour intervals, revealed minimal loss of iodine-containing compounds as each sample contained iodine [I] (total) at >1 ppmw levels.

EXAMPLE 1

In this example, the iodine removal zone was charged with Harshaw copper chromite 1186 (3 mm pellets, 50 mL) and the apparatus temperature was maintained at 180° C. throughout the experiment. An acetic acid stream containing 10 ppmw hydriodic acid (prepared as in Control Example 1) was passed through the apparatus at a rate of 13 mL (liquid) per hour. Samples were collected and analyzed for total iodine content (typically found to be <5 ppbw) and copper (typically found to be 11–19 ppmw). This example shows that in the absence of concurrent hydrogen flow, iodine removal is effective but copper migrates from the catalyst bed into the product stream.

EXAMPLE 2

The procedure described in Example 1 was repeated except that an 8% hydrogen in nitrogen mixture was passed (50 mL per minute) through the apparatus. concurrently with the acetic acid carboxyl stream. In this instance, the treated acetic acid stream was found to contain <1 ppmw of copper and <5 ppbw total iodine. In the presence of concurrent hydrogen flow, the removal of iodine containing impurities was effective and copper does not migrate into the product stream.

EXAMPLE 3

The procedure described in Example 2 was repeated except that the iodine removal zone was charged with Calsicat copper chromite E403 catalyst (50 mL). Effluent samples were found to contain <5 ppbw total iodine.

EXAMPLE 4

The procedure described in Example 3 was repeated except that the temperature within the iodine removal zone was held first at 200° C. and then at 160° C. Effluent samples were found to contain <5 ppbw total iodine. This example demonstrates that effective removal of iodine-containing impurities occurs over a substantial range of temperatures.

EXAMPLE 5

The procedure described in Example 2 was repeated except that the distillation zone was charged with Englehard copper chromite Cu-1920T (50 mL) and the acetic acid stream fed to the apparatus contained 0.81 weight percent hydriodic acid (prepared as in Control Example 1). Effluent samples were found to contain <5 ppbw total iodine and <1 ppmw copper. Thus, iodine removal is effective with relatively high concentrations of iodine-containing impurities in the feed stream.

EXAMPLE 6

The procedure described in Example 5 was repeated except that the acetic acid feed stream contained 10 ppmw hydriodic acid (prepared as in Example 1) and 1 weight percent water. The effluent stream was found to contain <30 ppbw total iodine. This example shows that the presence of water has no significant effect on the capability of the process to remove iodine-containing impurities from an acetyl feed stream.

EXAMPLE 7

The procedure described in Example 5 was repeated except that the acetic acid feed stream contained 10 ppmw hydriodic acid and 1 weight percent methyl acetate. The effluent stream was found to contain <20 ppbw total iodine. Thus, the process of this invention is capable of substantially reducing the level of iodine-containing impurities when the feed stream contains methyl acetate.

EXAMPLE 8

The procedure of Example 5 was repeated except that the acetic acid feed stream contained 10 ppm hydriodic acid and 1 weight percent acetic anhydride. The effluent stream was found to contain <30 ppbw total iodine. This example demonstrates that the present purification process is capable of reducing substantially the level of iodine-containing impurities when the feed stream contains acetic anhydride.

EXAMPLE 9

The procedure described in Example 5 was repeated except that the feed stream consisted of acetic anhydride containing <0.2 weight percent acetic acid and 11 ppmw hydriodic acid. The effluent stream was found to contain <20 ppbw total iodine. The present purification process is capable of substantially reducing the level of iodine-containing impurities in acetic anhydride-containing acetyl streams.

EXAMPLE 10

The procedure described in Example 2 was repeated except that a mixture of a copper-titania catalyst (10% copper content) (25 mL, see U.S. Pat. No. 4,929,777) and quartz chips (25 mL) was placed in the distillation zone. Effluent samples were found to contain <5 ppbw total iodine.

EXAMPLE 11

The procedure described in Example 2 was repeated except the iodine removal zone was charged with a copper-titania on silica catalyst (30% copper content) (50 mL, see U.S. Pat. No. 4,929,777). Effluent samples were found to contain <5 ppbw total iodine.

EXAMPLE 12

The procedure of Example 11 was repeated except that the acetic acid feed stream contained methyl iodide (11 ppm) and no hydriodic acid. Effluent samples were found to contain <5 ppbw total iodine. The process of the invention thus effectively reduces the level of iodine attributable to alkyl iodide in the feed stream.

EXAMPLE 13

The procedure described in Example 2 was repeated except (1) the iodine removal zone was charged with a Davison copper on silica (10% copper content, SMR-7-6826) catalyst (25 mL) and (2) in place of the 8% hydrogen in nitrogen gaseous stream, hydrogen was passed through the iodine removal zone at a rate of 20 mL per minute concurrently with the acetic acid feed at 15 mL (liquid) per hour. Effluent samples were found to contain <20 ppbw total iodine. This example illustrates that the purification process is tolerant of changes in the composition of the gaseous feed.

EXAMPLE 14

The procedure described in Example 2 was repeated except that a Davison copper on silica (10% copper content, SMR-7-6828) catalyst (25 mL) was placed in the iodine removal zone and the acetic acid feed stream fed at a rate of 24 mL per hour contained phenyl iodide (5 ppm) and no hydriodic acid. A hydrogen stream (20 mL/min) was passed over the catalyst bed concurrently with the acetic acid feed. Effluent samples were found to contain <6 ppb phenyl iodide. The present process thus is found to have effectively reduced the level of aryl iodide in the feed stream.

EXAMPLE 15

The procedure described in Example 2 was repeated except that a copper woven gauze (Goodloe packing material, 32 mL) was placed in the iodine removal zone and the acetic acid feed stream was adjusted to a flow rate of approximately 45 mL (liquid) per hour. Effluent samples were found to contain 150 ppbw total iodine indicating that copper gauze effects a reduction in iodine-containing impurities.

EXAMPLE 16

The procedure employed in Example 4 was repeated except that the iodine removal zone was charged with an Englehard copper on alumina (10% copper content, Cu-0226S) catalyst (25 mL) and the acetic acid feed stream was adjusted to a flow rate of approximately 35 mL (liquid) per hour. Effluent samples were found to contain <5 ppb total iodine.

EXAMPLE 17

The procedure of Example 16 was repeated except that a liquid phase acetic acid feed stream was passed through the iodine removal Zone at a flow rate of 35 mL (liquid) per hour while the temperature of the distillation zone was maintained at 80° C. Effluent samples were found to contain 8 ppb total iodine. The method effectively removes iodine from liquid phase acetyl product streams.

EXAMPLE 18

The procedure described in Example 2 was repeated except that the iodine removal zone was charged with an Englehard copper on alumina (50% copper content, Cu-0825T) catalyst (25 mL) and the acetic acid feed stream was adjusted to a flow rate of approximately 35 mL per hour. Effluent samples were found to contain <5 ppb total iodine.

EXAMPLE 19

The procedure of Example 18 was repeated except that the acetic acid feed stream was adjusted to a flow rate of approximately 114 mL (liquid) per hour. Effluent samples were found to contain <5 ppb total iodine. The flow rate of the stream being treated may be adjusted over a wide range and the iodine removal process remains effective.

EXAMPLE 20

In this example the iodine removal zone was constructed from a 25.4 cm section of 316 stainless steel tubing having an interior diameter of 13 mm. An Englehard copper on carbon (10% copper content, S. N. 907A-1-6-1) catalyst (11.1 g) was placed in the iodine removal zone. Using the general procedure employed in Example 4, acetic acid, containing 1616 ppmw iodine as hydriodic acid, was fed to the apparatus at a rate of 23-35 mL (liquid) per hour while maintaining the temperature of the copper on carbon catalyst at 180° C. A 10% hydrogen in nitrogen mixture was concurrently passed through the bed at a rate of 150 mL per minute. Effluent samples were found to contain <20 ppb total iodine. When the copper on carbon catalyst was omitted from the iodine removal zone, the effluent contained 400–600 ppm total iodine.

EXAMPLE 21

The iodine removal zone was charged with Calsicat copper chromite E406TR (33.6% copper content, 20 mL) and the apparatus temperature was maintained at 180° C. throughout the experiment. Care was taken to exclude all sources of oxygen contamination. An acetic acid stream containing 10 ppmw hydriodic acid (prepared as in Control Example 1) was passed through the apparatus at 13 mL (liquid) per hour. A nitrogen gas stream (50 mL/min) was passed through the reactor concurrently with the acetic acid carboxyl stream. Samples were collected and analyzed for total iodine content (typically found to be <10 ppbw) and copper (typically found to be <0.5 ppmw). This example shows that in the absence of concurrent hydrogen flow and with careful elimination of all oxygen contaminants, iodine removal is effective and copper does not contaminate the product solution.

EXAMPLE 22

The iodine removal zone was charged with Davison copper on silica (10% copper content, SMR-7-6826) catalyst (20 mL) and the apparatus temperature was maintained at 180° C. throughout the experiment. Care was taken to exclude all sources of oxygen contamination. An acetic acid stream containing 10 ppmw hydriodic acid (prepared as in Control Example 1) was passed through the apparatus at 13–15 mL (liquid) per hour. This experiment was conducted for 90 hours. A nitrogen gas stream (50 mL/min) was passed through the reactor concurrently with the acetic acid carboxyl stream during all but 12 hours in the middle of the run when a hydrogen gas stream (20 mL/min) was passed concurrently through the reactor. Samples were collected and analyzed for total iodine content (typically found to be between 10 and 80 ppbw) and copper content (typically found to be between 0.5 and 2.9 ppmw). No variation in either iodine or copper content of the product could be attributed to the presence or absence of hydrogen in the gaseous stream.

The invention has been described in detail with particular reference to preferred embodiments thereof, but it will be understood that variations and modifications may be effected within the spirit and scope of the invention.

We claim:

1. Process for the reduction in the iodine content of a crude carboxyl product stream comprising (i) one or more carboxyl compounds selected from carboxylic acids, carboxylic anhydrides and alkylidene dicarboxylates and (ii) iodine, one or more iodine-containing compounds or a mixture thereof, which comprises the steps of:
   (1) contacting the crude carboxyl product stream with a copper-containing, scavenger material in an iodine removal zone; and
   (2) removing from the iodine removal zone a refined carboxyl product stream containing less iodine than the crude carboxyl stream.

2. Process according to claim 1 wherein the crude carboxyl product stream contains about 500 parts per billion by weight to 250 parts per million by weight iodine and the refined carboxyl product stream contains less than about 200 parts per billion iodine.

3. Process according to claim 2 wherein the iodine removal zone is maintained at a temperature of about 20° to 275° C. and at a pressure of about 0.25 to 10 bars absolute.

4. Process for the reduction in the iodine content of a crude acetyl product stream comprising (i) acetic acid, acetic anhydride, a mixture of acetic acid and acetic anhydride, or a mixture of acetic acid, acetic anhydride and ethylidene diacetate and (ii) 500 parts per billion by weight to 250 parts per million by weight iodine present as iodine, one or more iodine-containing compounds or a mixture thereof, which comprises the steps of:
   (1) contacting the crude carboxyl product stream with a copper-containing, scavenger material in an iodine removal zone at a temperature of about 80° to 250° C.; and
   (2) removing from the iodine removal zone a refined carboxyl product stream containing less than 20 parts per billion by weight iodine.

5. Process according to claim 4 wherein the crude carboxyl product stream comprises acetic acid, Step (1) is carried out at a temperature of about 80° to 250° C. and the copper-containing, scavenger material is selected from copper chromite and copper supported on a catalyst support material.

6. Process for the reduction in the iodine content of a crude carboxyl product stream comprising (i) one or more carboxyl compounds selected from carboxylic acids, carboxylic anhydrides and alkylidene dicarboxylates and (ii) iodine, one or more iodine-containing compounds or a mixture thereof, which comprises the steps of:
   (1) contacting a vapor of the crude carboxyl product stream with a copper-containing, scavenger material in an iodine removal zone; and
   (2) removing from the iodine removal zone a vapor of a refined carboxyl product stream containing less iodine than the crude carboxyl stream.

7. Process according to claim 6 wherein the crude carboxyl product stream contains about 500 parts per billion by weight to 250 parts per million by weight iodine and the refined carboxyl product stream contains less than about 200 parts per billion iodine.

8. Process according to claim 7 wherein the iodine removal zone is maintained at a temperature of about 120° to 250° C. and at a pressure of about 0.25 to 10 bars absolute.

9. Process for the reduction in the iodine content of a crude acetyl product stream comprising (i) acetic acid, acetic anhydride, a mixture of acetic acid and acetic anhydride, or a mixture of acetic acid, acetic anhydride and ethylidene diacetate and (ii) 500 parts per billion by weight to 250 parts per million by weight iodine present as iodine, one or more iodine-containing compounds or a mixture thereof, which comprises the steps of:
   (1) contacting a vapor of the crude carboxyl product stream with a copper-containing, scavenger material in an iodine removal zone at a temperature of about 120° to 250° C.; and
   (2) removing from the iodine removal zone a vapor of a refined carboxyl product stream containing less than 20 parts per billion by weight iodine.

10. Process according to claim 9 wherein the crude carboxyl product stream comprises acetic acid, Step (1) is carried out at a temperature of about 120° to 250° C. and the copper-containing, scavenger material is selected from copper chromite and copper supported on a catalyst support material.

11. Process for the reduction in the iodine content of a crude carboxyl product stream comprising (i) one or more carboxyl compounds selected from carboxylic acids, carboxylic anhydrides and alkylidene dicarboxylates and (ii) iodine, one or more iodine-containing compounds or a mixture thereof, which comprises the steps of:
   (1) contacting a vapor of a mixture of the crude carboxyl product stream and hydrogen with a copper-containing, scavenger material in an iodine removal zone; and
   (2) removing from the iodine removal zone a vapor of a refined carboxyl product stream containing less iodine than the crude carboxyl stream.

12. Process according to claim 11 wherein the crude carboxyl product stream contains about 500 parts per billion by weight to 250 parts per million by weight iodine and the refined carboxyl product stream contains less than about 200 parts per billion iodine.

13. Process according to claim 12 wherein the iodine removal zone is maintained at a temperature of about 80° to 250° C. and at a pressure of about 0.25 to 10 bars absolute.

14. Process for the reduction in the iodine content of a crude acetyl product stream comprising (i) acetic acid, acetic anhydride, a mixture of acetic acid and acetic anhydride, or a mixture of acetic acid, acetic anhydride and ethylidene diacetate and (ii) 500 parts per billion by weight to 250 parts per million by weight iodine present as iodine, one or more iodine-containing compounds or a mixture thereof, which comprises the steps of:

(1) contacting a vapor of a mixture of the crude carboxyl product stream and hydrogen with a copper-containing, scavenger material in an iodine removal zone at a temperature of about 120° to 250° C.; and (2) removing from the iodine removal zone a vapor of a refined carboxyl product stream containing less than 20 parts per billion by weight iodine.

15. Process for the reduction in the iodine content of a crude acetic acid product stream comprising (i) acetic acid and (ii) 500 parts per billion by weight to 250 parts per million by weight iodine present as iodine, one or more iodine-containing compounds or a mixture thereof, which comprises the steps of:

(1) contacting a vapor of a mixture of the crude acetic acid stream and hydrogen with a copper-containing, scavenger material selected from copper chromite and copper supported on a catalyst support material in an iodine removal zone at a temperature of about 120° to 250° C.; and (2) removing from the iodine removal zone a vapor of a refined acetic acid stream containing less than 20 parts per billion by weight iodine.

* * * * *